United States Patent
Iwata et al.

(10) Patent No.: US 12,083,210 B2
(45) Date of Patent: Sep. 10, 2024

(54) MULTI-FUNCTION HAIR CARE COMPOSITION

(71) Applicant: The Procter & Gamble Company, Cincinnati, OH (US)

(72) Inventors: Toshiyuki Iwata, Singapore (SG); Supriya Punyani, Singapore (SG); Kai Wei Kelvin Lee, Singapore (SG); Junji Hamano, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/838,360

(22) Filed: Jun. 13, 2022

(65) Prior Publication Data
US 2022/0401333 A1    Dec. 22, 2022

Related U.S. Application Data

(60) Provisional application No. 63/210,510, filed on Jun. 15, 2021.

(51) Int. Cl.

| | |
|---|---|
| *A61K 8/49* | (2006.01) |
| *A61K 8/34* | (2006.01) |
| *A61K 8/362* | (2006.01) |
| *A61K 8/365* | (2006.01) |
| *A61K 8/368* | (2006.01) |
| *A61K 8/42* | (2006.01) |
| *A61K 8/73* | (2006.01) |
| *A61Q 5/00* | (2006.01) |
| *A61Q 5/12* | (2006.01) |

(52) U.S. Cl.
CPC ............ *A61K 8/4926* (2013.01); *A61K 8/342* (2013.01); *A61K 8/362* (2013.01); *A61K 8/365* (2013.01); *A61K 8/368* (2013.01); *A61K 8/42* (2013.01); *A61K 8/73* (2013.01); *A61K 8/731* (2013.01); *A61Q 5/006* (2013.01); *A61Q 5/12* (2013.01); *A61K 2800/34* (2013.01)

(58) Field of Classification Search
CPC ...... A61K 8/4926; A61K 8/342; A61K 8/362; A61K 8/365; A61K 8/368; A61K 8/42; A61K 8/73; A61K 8/731; A61K 2800/34; A61K 8/44; A61K 8/60; A61K 8/732; A61K 8/737; A61K 2800/262; A61Q 5/006; A61Q 5/12
See application file for complete search history.

(56) References Cited

U.S. PATENT DOCUMENTS

| | | | |
|---|---|---|---|
| 9,993,404 B2 | 6/2018 | Callens et al. | |
| 2002/0168327 A1 | 11/2002 | Bailey et al. | |
| 2003/0228404 A1* | 12/2003 | Nishimoto | C07H 3/04 426/548 |
| 2010/0278759 A1* | 11/2010 | Murad | A61K 8/062 424/59 |
| 2011/0268684 A1* | 11/2011 | Battermann | A61K 8/4946 514/396 |
| 2014/0120048 A1 | 5/2014 | Krueger | |
| 2015/0150779 A1* | 6/2015 | Delowsky | A61K 8/8152 424/70.11 |
| 2018/0092832 A1* | 4/2018 | Holmes | A61K 8/361 |
| 2019/0000735 A1* | 1/2019 | Kelly | A61K 8/4906 |
| 2020/0108003 A1 | 4/2020 | Iwata et al. | |
| 2020/0129398 A1 | 4/2020 | Reay et al. | |
| 2020/0146955 A1* | 5/2020 | Zhao | A61K 8/416 |
| 2020/0323758 A1* | 10/2020 | Karagianni | A61K 8/922 |
| 2021/0069091 A1* | 3/2021 | Oh | A61K 8/27 |
| 2022/0226797 A1* | 7/2022 | Popplewell | C08L 89/00 |
| 2022/0251393 A1* | 8/2022 | Imoto | A61K 8/0279 |
| 2023/0133580 A1* | 5/2023 | Yamada | A23L 33/105 514/785 |

FOREIGN PATENT DOCUMENTS

| | | |
|---|---|---|
| EP | 1855645 A2 | 11/2007 |
| WO | 02100360 A1 | 12/2002 |
| WO | 2012055585 A1 | 5/2012 |
| WO | 2016172412 A1 | 10/2016 |
| WO | 2020229203 A1 | 11/2020 |

OTHER PUBLICATIONS

Kao Corporation, 2019 chemical.kao.com/content/dam/sites/kao/chemical-kao-com/global/pdf/sustainability/saicm/article_05/SafetySummary_glen_QAC.pdf (Year: 2019).*
Cherney, 2020 healthline.com/health/salicylic-acid-shampoo (Year: 2020).*
Freitas-Seitz, 2019 beautylish.com/a/vzais/what-are-phas-polyhydroxy-acids-skincare (Year: 2019).*
McKay, 2005 naturallycurly.com/curlreading/curl-products/polymers-in-hair-care-products (Year: 2005).*
SpecialChem, 2020 cosmetics.specialchem.com/centers/selecting-the-right-surfactant-for-cosmetics/surfactants-in-hair-care-applications (Year: 2020).*
Anveya, 2020 anveya.com/blogs/top-tips/prevalence-of-polyquaternium-10-in-skincare-and-haircare (Year: 2020).*
Chung et al. 2015, ncbi.nlm.nih.gov/pmc/articles/PMC4563105/ (Year: 2015).*
Ahn et al. 2020, ncbi.nlm.nih.gov/pmc/articles/PMC7766712/ (Year: 2020).*
16055 PCT Search Report and Written Opinion for PCT/US2022/033538 dated Oct. 28, 2022, 15 pages.

* cited by examiner

*Primary Examiner* — Lezah Roberts
*Assistant Examiner* — Abdulrahman Abbas
(74) *Attorney, Agent, or Firm* — John G. Powell; Kathleen Y. Carter

(57) ABSTRACT

A translucent hair care composition comprising a substituted 2-pyridinol-N-oxide material, a cationic surfactant, a fatty alcohol, a water-soluble polymer, water, and a monocarboxylic acid.

15 Claims, No Drawings

MULTI-FUNCTION HAIR CARE COMPOSITION

FIELD OF THE INVENTION

The present invention relates to a multi-function hair care composition.

BACKGROUND OF THE INVENTION

For years, anti-dandruff shampoos have been widely used to treat dandruff and to clean hair and scalp. However, for consumers who have severe dandruff issues, such as flaking, itching, or an oily or dry scalp, using only anti-dandruff shampoo is often not enough. This is because the deposition, or delivery of anti-dandruff active to the scalp is limited by use of just a single product. While there have been anti-dandruff conditioners in the market for many years, these rinse-off anti-dandruff conditioners are highly viscous and greasy-looking products. In fact, these products are often just regular hair conditioning products with anti-dandruff actives added in. As a result, most consumers apply these products carefully to their hair, while intentionally avoiding the products from touching their scalps, meaning the consumers do not receive the anti-dandruff benefit of the products. The leave-on anti-dandruff conditioners are in various forms, such as spray tonics, lotions, and creams, but the problem with these products is that, while they may deliver an anti-dandruff benefit, their hair conditioning is very poor. Indeed, most of them are harmful to hair conditioning, such as increasing friction or leaving sticky or greasy material on the hair. Therefore, consumers cannot use these products every day, and these products are less popular in the market. Therefore, there is a need for conditioners that are multi-functional, that is, that consumers can apply to their scalp delivering anti-dandruff efficacy while still providing hair conditioning that consumers expect and want.

In addition, consumers desire a minimal number of ingredients in their products and want to understand why each ingredient is needed. Many consumers look for labels stating the compositions are free of unnecessary chemicals, particularly for products that are applied directly to the scalp, which may already be sensitive due to the flaking and itching symptoms of dandruff. It follows then that formulators must work to eliminate or minimize the number of ingredients that are not primarily functional to the consumer benefits, for example, preservatives, stabilizers, or solvents.

Therefore, there is a continuing need for conditioners that offer not only anti-dandruff benefits, but that provide hair conditioning that improves the feel, appearance, and manageability of hair, all while being formulated with natural and multi-functional materials.

SUMMARY OF THE INVENTION

A translucent hair care composition comprising:
a) substituted 2-pyridinol-N-oxide material;
b) a cationic surfactant having melting point higher than 40° C.;
c) a fatty alcohol having a melting point higher than 40° C.;
d) a water-soluble polymer, wherein the water-soluble polymer has a natural origin backbone selected from the group consisting of cellulose, starch, guar, and gellan;
e) water; and
f) a monocarboxylic acid;

wherein the composition has a pH from about 3.5 to about 6.0;
wherein the composition has a light transmittance percent measured at 600 nm greater than 10%; and
wherein the viscosity is from about 10 Pa·s to about 100 Pa·s.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

The term "molecular weight" or "M.Wt." as used herein refers to the weight average molecular weight unless otherwise stated.

"QS" means sufficient quantity for 100%.

"Substantially free of" refers to about 2% or less, about 1% or less, or about 0.1% or less of a stated ingredient. "Free of" refers to no detectable amount of the stated ingredient or thing.

Hair Care Composition

The present inventive hair care compositions provide a combination of multi-functional ingredients that can deliver multiple benefits, including anti-dandruff, anti-itch, soothing, fragrance, preservation, wet and dry conditioning, all while having nine or fewer ingredients. The product viscosity may be between a cream and a lotion, and the color may be translucent. When the present inventors set out to solve the problem of providing hair care compositions that delivered the numerous benefits described while not having very many ingredients, they realized that single ingredients must serve multiple functions. They further desired to formulate with consumer-preferred natural ingredients. For example, the surfactant stearylamidopropyl dimethylamine (stearamidopropyl dimethylammonium), SAPDMA, is naturally derived and has a tertiary amine headgroup, which allows a formulator freedom to choose the acid to protonate it (to turn it to cationic surfactant). Further, salicylic acid may be chosen, which then reduces or eliminates the need to add a preservative.

Anti-Dandruff Active

Piroctone and salts of piroctone, such as piroctone olamine, are known to provide anti-dandruff benefit. However, piroctone olamine is often supplied as a crystal powder, and is also known to have very limited solubility in water, meaning the challenge is to assure solubilization of an anti-dandruff active in as simple as possible a material combination.

It has been found by the present inventors that certain solid organic compounds, such as piroctone and/or salts thereof, tend to crystallize in the following conditions:

when the aqueous composition comprises cationic surfactant and high melting point fatty compounds;

when the amount of the solid organic compounds increases in the composition, especially 0.2% or above; and/or when the composition has pH of from about 3.5 to about 6.

Piroctone olamine in a conditioner is usually solubilized by some type of oil at high concentration (around 5%). The oil is typically emulsified by a cationic surfactant and high melting point fatty compounds, resulting in a highly viscous and opaque product. In contrast, the present invention does not use such oil (which causes the hair and scalp to become oily), and instead uses a specific surfactant body, such as SAPDMA, and a specific acid as the counterion, in a specific ratio of the surfactant body/acid/piroctone olamine, to get to a desired pH range for the piroctone olamine to function and deposit better on the scalp. This leads to anti-dandruff efficacy and good conditioning, while not using too much of the cationic surfactant and high melting point fatty compounds.

In some embodiments, the anti-dandruff active may be a substituted 2-pyridinol-N-oxide material, such as piroctone olamine or ciclopirox olamine Piroctone olamine and ciclopirox olamine are the salt of piroctone and ciclopirox, respectively, with monoethanolamine. In the compositions having an acidic pH, they become protonated to become piroctone and ciclopirox, respectively. In the present invention, the composition preferably has an acidic pH, more preferably has a pH from about 2 to about 6, still more preferably from about 3.5 to about 6, further more preferably from about 3.5 to about 5.

The present invention may also include one or more soluble scalp health actives, which may be one material or a mixture selected from the groups consisting of: azoles, such as climbazole, ketoconazole, itraconazole, econazole, and elubiol; hydroxy pyridones, such as piroctone olamine, ciclopirox, rilopirox, and MEA-Hydroxyoctyloxypyridinone; strobilurins such as azoxystrobin and metal chelators such as 1,10-phenanthroline.

The azole soluble scalp health active may be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. The azole soluble scalp health active may be ketoconazole. The sole soluble scalp health active may be ketoconazole.

These anti-dandruff and scalp health active compounds are not soluble in a typical solvent such as water or an aqueous mixture such as water containing even a high level of glycerin or propylene glycol. They typically require either a high level (greater than 5% or even greater than 10%) of an emollient oil, such as triethylhexanoine, octyldodecyl myristate, or a high level (greater than 50%) of an alcohol, such as ethanol. The former (oil) is known to cause an oily feel that is a negative on the scalp and hair, and for the latter (alcohol), it is known that most consumers are afraid to apply it to a scalp that is already sensitive due to dandruff symptoms. The present invention solubilizes such anti-dandruff actives by the combination of a surfactant (primarily needed for hair conditioning), and a specific acid (primarily needed to adjust pH). Nothing other than these two materials are required to formulate these anti-dandruff and scalp health actives into soluble form in a liquid.

Any of the anti-dandruff or other scalp actives may be in the composition in an amount from about 0.01% to about 2%, by weight of the composition.

Cationic Surfactant

The hair care composition of the present invention may comprise a cationic surfactant. In some embodiments, the cationic surfactant may be stearylamidopropyl dimethylamine (stearamidopropyl dimethylammonium), SAPDMA.

The ratio of cationic surfactant to anti-dandruff active may be 2.4 to 6.2 (wt/wt) (or 2 to 5 (mol/mol)), preferably 3.1 to 5.5 (wt/wt) (or 2.5 to 4.5 (mol/mol)), or may be from 3.0 to 4.0 (mol/mol). Outside of this ratio may result in crystallization of the piroctone olamine that is left in the composition, or the piroctone concentration may be too low to be efficacious, or the surfactant may be too high, or the composition may be too greasy.

The cationic surfactant can be one cationic surfactant or a mixture of two or more cationic surfactants. Preferably, the cationic surfactant system is selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt. More preferably, the cationic surfactant system is a mixture of mono-long alkyl quaternized ammonium salt and di-long alkyl quaternized ammonium salt. The choice of anion as counterion to make the surfactant a salt will be discussed in the later section titled "Acid".

Mono-Long Alkyl Quaternized Ammonium Salt

The monoalkyl quaternized ammonium salt cationic surfactants useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

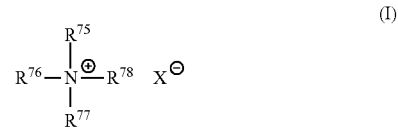

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^{-}$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of the acid discussed, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, salicylic acid, lactic acid, hydrochloric acid, malic acid, succinic acid, acetic acid, fumaric acid, tartaric acid, glycolic acid, aspartic acid, citric acid, l-glutamic hydrochloride, maleic acid, lactobionic acid or glucolactone and mixtures thereof; more preferably salicylic acid, l-glutamic acid, lactic acid, aspartic acid, glycolic acid, lactobionic acid or glucolactone. The amines herein are preferably partially neutralized with any of the acids at a molar ratio of the amine to the acid of from about 1:1 to about 1:4, more preferably from about 1:1.1 to about 1:3.2.

Di-Long Alkyl Quaternized Ammonium Salt

Di-long alkyl quaternized ammonium salt is preferably combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of preferably from about 10% to about 50%, more preferably from about 30% to about 45%.

The dialkyl quaternized ammonium salt cationic surfactants useful herein are those having two long alkyl chains having 12-30 carbon atoms, preferably 16-24 carbon atoms, more preferably 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

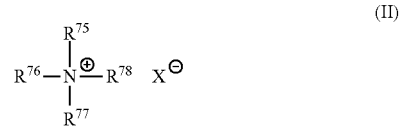

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

High Melting Point Fatty Compound

The composition of the present invention may comprise a high melting point fatty compound. The high melting point fatty compound is included in the composition at a level of preferably from about 0.1% to about 20%, more preferably from about 1% to about 15%, still more preferably from about 1.5% to about 8% by weight of the composition, The high melting point fatty compound useful herein have a melting point of 25° C. or higher to 60° C., preferably a melting point of 30° C. to 60° C., in some embodiments a melting point of 40° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability when the consumer rinses off the composition.

Aqueous Carrier

The hair care composition of the present invention comprises an aqueous carrier. The level and species of the carrier are selected according to the compatibility with other components, and other desired characteristics of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, pentylene glycol, hexylene glycol, and glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 30% to about 95%, and more preferably from about 80% to about 95% water.

Gel Matrix

Preferably, in the composition of the present invention, a cationic surfactant, a high melting point fatty compound, and an aqueous carrier form a gel matrix.

The gel matrix is suitable for providing various conditioning benefits, for example, hair conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6. For improved deposition of the solid organic compound on hair, face, body and/or scalp, it may be preferred that the weight ratio of the cationic surfactant to the high melting point fatty compound is in the range of, preferably from about 1:1 to about 1:4.

Water-Soluble Polymer

The hair care compositions of the present invention may comprise a water-soluble polymer. A hydrophobically modified polymer may be used while the overall concentration of the lamellar gel phase is low, in order to adjust viscosity of the composition. The hydrophobically-modified water-soluble polymer may have a natural origin backbone such as cellulose, starch, guar, gellan, etc., plus combinations thereof, but is not limited to these. A natural origin backbone here may mean a polymer that is water soluble and biodegradable. The water-soluble polymer may have a cationic charge. In some embodiments the water-soluble polymer may be polyquaternium-10, such as UCARE Extreme Polymer supplied by Dow Inc., or may be cetyl hydroxyethylcellulose, such as Polysurf 67 CS or Natrosol 330 PLUS CS, both supplied by Ashland. A polymer may be used that can help restore hydrophobicity of the hair surface, due to higher hydrophobicity of the polymer itself.

The compositions of the present invention may comprise from about 0.1% to about 1.5% of the water-soluble polymer, preferably 0.2 to 1.0%.

Acid

The hair care compositions of the present invention may comprise an acid. The acid may be used to control the pH of the composition to the desired range (3.5 to 6), because otherwise, the pH may be higher than 7 due to the presence of tertiary amine surfactant and piroctone olamine.

The acid can be pre-paired with the surfactant body to form a quaternary ammonium salt or a tertiary amine salt, and supplied by the surfactant supplier.

Use of SAPDMA as a surfactant allows for a choice to be made as to what acid to use to protonate the surfactant to turn it to a cationic surfactant. In some embodiments, the acid may be an α-hydroxy acid (AHA), a β-hydroxy acid (BHA), or a polyhydroxy acid (PHA). A BHA may be salicylic acid, which reduces or eliminates the need to add a preservative. In some embodiments, the acid may be lactic acid and glycolic acid (both α-hydroxy acids) instead of salicylic acid. Polyhydroxy acids used may be lactobionic acid or gluconolactone. Other acids that may be used are ones having net −1 charge as their dominant species in the final pH of the composition, such as glutamic acid or aspartic acid, but likely require a preservative in the composition. Acids to avoid are polyvalent acids such as maleic acid, oxalic acid, citric acid, EDTA, malic acid, tartaric acid, etc, and the compositions of the present invention may be free of these materials, as the resulting compositions generally will not be translucent. In some embodiments, combinations or mixtures of acids may be used.

The ratio of the acid to the sum of the (cationic surfactant and anti-dandruff active) may be from about 0.4 to about 1.12 (wt/wt) (1.0 to 2.0 (mol/mol)). Ratios lower than this typically lead to a crystal presence, while higher ratios than this can lead to the pH being too low.

The composition may be substantially free of an acid other than the one to protonate the cationic surfactant body.

In general, the levels or amounts in the composition for the acid are determined by the mole to mole ratio parameters. But for salicylic acid, for example, the amount may be from about 0.2 to about 3.6%, or from about 0.25% to about 3.3%, or from about 0.25 to about 1.3%, by weight of the composition.

Fragrance

The compositions of the present invention may comprise a fragrance, or combination of fragrances. Some fragrances may comprise, multiple fragrance ingredients. In particular, the fragrance may comprise hinokitiol, phenoxyethanol, and L-menthol. The compositions may comprise the fragrance at the level solely required to design the desired fragrance character and strength, but not at a higher enough level that any of the materials act as a preservative for the composition.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolyzed collagen with tradename Peptein 2000 available from Hormel, vitamin E with tradename Emix-d available from Eisai, panthenol available from Roche, panthenyl ethyl ether available from Roche, hydrolyzed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; perfumes; and sequestering agents, such as disodium ethylenediamine tetra-acetate; and ultraviolet and infrared screening and absorbing agents such as octyl salicylate.

In some embodiments, the compositions of the present invention may be free of preservatives. In some embodiments, the compositions of the present invention may be free of preservative compounds such as phenoxyethanol, benzyl alcohol, methyl paraben, ethyl paraben, and/or propyl paraben. While phenoxyethanol may be used as a fragrance at a level of at most 0.1%, by weight of the composition, it may not be used as a preservative, which would be at a level of at least 0.25%, by weight of the composition.

In some embodiments the composition may be free of a liquid oily compound having an A log P≥5.5.

Product Forms

The compositions of the present invention can be in the form of rinse-off products or leave-on products and can be formulated in a wide variety of product forms, including but not limited to creams, gels, emulsions, mousses and sprays.

The conditioning composition of the present invention is especially suitable for rinse-off hair conditioner. Such compositions are preferably used by following steps:
  (i) after shampooing hair, applying to the hair an effective amount of the conditioning compositions for conditioning the hair; and
  (ii) then rinsing the hair.

Translucence

The hair care compositions of the present invention may be translucent. A composition is determined to be translucent or not by the light transmittance test described below. The inventive compositions may have a light transmittance percent measured at 600 nm greater than about 10%, in some embodiments at least greater than 2%. The translucence of the compositions may be consumer-preferred and can be a signal to apply to the scalp, leading to the anti-dandruff benefits.

The inventive compositions may have a viscosity from about 1 Pa·s to about 500 Pa·s, preferably from about 10 Pa·s to about 100 Pa·s. The lower viscosity compositions are more likely to be used on the scalp by consumers, thus more likely to result in anti-dandruff efficacy.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Table 1 below shows Inventive Examples 1-7.

TABLE 1

|  | Ex.1 | Ex.2 | Ex.3 | Ex.4 | Ex.5 | Ex.6 | Ex.7 |
|---|---|---|---|---|---|---|---|
| Deionized Water | q.s. | q.s. | q.s. | q.s. | q.s. | q.s. | q.s |
| Glycerine |  |  | 50.00 |  |  |  |  |
| Cetyl Hydroxyethylcellulose [1] |  |  |  |  |  | 1.00 |  |
| Cetyl Hydroxyethylcellulose [2] | 1.00 | 1.00 | 1.00 | 1.50 | 1.00 |  |  |
| Polyquaternium-10 [3] |  |  |  |  |  |  | 0.50 |
| Polyquaternium-37 [4] |  |  |  |  |  |  |  |
| Stearamidopropyl Dimethylamine | 1.24 | 1.24 | 2.47 | 1.24 | 1.24 | 1.24 | 2.00 |
| Laureth-9 | 2.00 | 2.00 | 2.00 | 2.00 | 2.00 | 2.00 | 2.00 |
| Cetearyl Alcohol | 1.24 | 1.24 | 2.47 | 1.24 | 1.24 | 1.24 | 3.00 |
| Triethylhexanoine |  |  |  |  |  |  |  |
| Piroctone Olamine | 0.25 | 0.25 | 0.50 | 0.25 | 0.25 | 0.25 | 0.25 |
| Sodium Benzoate |  |  |  |  |  |  |  |
| Pentylene Glycol |  | 6.00 |  | 6.00 | 6.00 | 6.00 |  |
| Salicylic Acid | 0.75 | 0.75 | 1.50 | 0.75 | 0.75 | 0.75 | 1.12 |
| L-Glutamic Acid |  |  |  |  |  |  |  |
| Fragrance Base | 0.40 | 0.80 | 0.90 | 0.90 | 0.90 | 0.90 | 0.25 |
| Hinokitiol | 0.10 | 0.10 |  |  |  |  | 0.05 |
| Magnonol |  | 0.10 |  |  |  |  |  |
| Phenoxyethanol | 0.10 |  | 0.10 |  |  |  | 0.05 |
| Benzyl Alcohol | 0.10 |  |  |  |  |  |  |
| L-Menthol | 0.30 |  |  |  |  |  | 0.15 |
| Phase stability | S | S | S | S | S | S | S |
| pH | 3.9 | 3.9 | 4.1 | 4.1 | 4.0 | 4.0 | 4.0-4.5 |
| Viscosity @ 0.2 s$^{-1}$ [Pa·s] | 92.6 | 23.5 | 67.6 | 48.5 | 21.0 | 30.1 | 10~100 |
| Light transmittance, % T600 | Tr | Tr | Tr | 26.2 | 33.3 | 27.3 | Tr |
| MST | pass | pass | pass | — | — | — | — |

Table 2 shows comparative examples. Comparative Examples 1, 4, and 5 do not have a water soluble polymer having a natural origin backbone selected from the group consisting of cellulose, starch, guar, and gellan. Comparative Example 3 also does not have a water-soluble polymer. As can be seen, all Comparative Examples are outside the range of one or more of a pH from about 3.5 to about 6.0; being translucent; and a viscosity of about 10 Pa·s to about 100 Pa·s.

TABLE 2

| | C. Ex. 1 | C. Ex. 3 | C. Ex. 4 | C. Ex. 5 |
|---|---|---|---|---|
| Deionized Water | q.s. | q.s. | q.s. | q.s. |
| Glycerine | | | | |
| Cetyl Hydroxyethylcellulose [1] | | | | |
| Cetyl Hydroxyethylcellulose [2] | | | | |
| Polyquaternium-10 [3] | | | | |
| Polyquaternium-37 [4] | 1.40 | | 0.70 | 0.70 |
| Stearamidopropyl Dimethylamine | 2.00 | 3.24 | 2.00 | 2.00 |
| Laureth-9 | | | 1.50 | 1.50 |
| Cetearyl Alcohol | 1.00 | 6.80 | 4.00 | 4.00 |
| Triethylhexanoine | | | | 5.00 |
| Piroctone Olamine | 0.25 | 0.25 | 0.25 | 0.25 |
| Sodium Benzoate | | 0.25 | | |
| Pentylene Glycol | | 0.60 | | |
| Salicylic Acid | 0.95 | | | 1.12 |
| L-Glutamic Acid | | 1.90 | 0.64 | |
| Fragrance Base | 0.35 | 1.00 | 0.70 | 0.70 |
| Hinokitiol | | | | |
| Magnonol | | | | |
| Phenoxyethanol | | | | |
| Benzyl Alcohol | | | | |
| L-Menthol | 0.15 | | 0.30 | 0.30 |
| Phase stability | S | S | U | S |
| pH | 3.7 | 4.5 | >6 | 3.5~6.0 |
| Viscosity @ 0.2 s$^{-1}$ [Pa · s] | 210.9 | 141.0 | — | — |
| Light transmittance, % T600 | 17.4 | Op | Op | Op |
| MST | pass | fail | — | — |

[1] Polysurf 67 CS from Ashland
[2] Natrosol PLUS 330 CS from Ashland
[3] UCARE Extreme Polymer from Dow Inc.
[4] Cosmedia Ultragel 300 from BASF Test Methods Process The water soluble polymer is dissolved in water. The polymer solution is heated up to 77° C. The cationic surfactant, fatty alcohol, 2-pyridinol-N-oxide material, and acid are added, and mixed until a homogeneous emulsion. The mixture is cooled down to about 35° C. while mixing. The fragrance is mixed in. The apparatus can be any kind of tank and agitator available in the market.

Phase Stability

Sample is stored in glass jar at room temperature. Visible phase separation is recorded after 1 month. The same samples were observed by microscope with crossed-polarizer filter for the presence of Piroctone Olamine crystal. S=Stable, U=Unstable.

Viscosity

Viscosity is measured by shear rate ramp method with a rheometer available from TA Instruments with a model name DHR-2. Geometry is cone-plate, with the 40 mm diameter 2 degree cone angle with designated gap by the specific cone (typically 50 μm). Shear rate is logarithmically increased from 0.1 to 1100 s$^{-1}$ in 1 min, and temperature is kept at 26.7° C. The viscosity at shear rate=0.2 s$^{-1}$ is read.

Light Transmittance

Light transmittance of sample is measured within a day of sample making A % light transmittance at wave length 600 nm of the sample of 1 cm light path length is measured by xRite Ci7800 Spectrophotometer. Some of the results are not quantitative but are shown as translucent (Tr) or opaque (Op).

Microbial Susceptibility Test (MST)

2 separate pools of challenge organisms, Bacterial pool: *Staphylococcus aureus*, *Pseudomonas aeruginosa*, *Escherichia coli*, *Burkholderia capacia*, *Klebsiella pneumoniae*, *Enterobacter gergoviae* and *Serratia marcescens*; Yeast and Mold pool: *Candida albicans* and *Aspergillus brasiliensis* were added to the diluted product to simulate potential consumer contaminations. The microbial challenge level in diluted product for each pool is $10^5$-$10^7$ CFU/g. The microbial content of the inoculated product was subsequently evaluated over the next four weeks at multiple time points using microbiological plate count. Serial dilution and preservative neutralization were accomplished with nutritive bases before plating. Product is deemed to have passed MST if the success criteria below are met:

| | Success Criteria | | | |
|---|---|---|---|---|
| | Day 2 | Day 7 | Day 14 | Day 28 |
| Bacteria | ≥2 log reduction | ≥3 log reduction | None | No increase from Day 7 |
| Yeast/Mold | None | | ≥2 log reduction | No increase from Day 14 |

EXAMPLES/COMBINATIONS

A. A translucent hair care composition comprising: a) a substituted 2-pyridinol-N-oxide material; b) a cationic surfactant having melting point higher than 40° C.; c) a fatty alcohol having a melting point higher than 40° C.; d) a water-soluble polymer, wherein the water-soluble polymer has a natural origin backbone selected from the group consisting of cellulose, starch, guar, and gellan; e) water; and f) a monocarboxylic acid; wherein the composition has a pH from about 3.5 to about 6.0; wherein the composition has a light transmittance percent measured at 600 nm greater than 10%; and wherein the viscosity is from about 10 Pa·s to about 100 Pa·s.

B. The composition of paragraph A, wherein the acid is selected from the group consisting of an α-hydroxy acid (AHA), a β-hydroxy acid (BHA), a polyhydroxy acid (PHA), and an aminoacid.

C. The composition of any one of paragraphs A or B, wherein the acid is a BHA and is salicylic acid.

D. The composition of paragraph B, wherein the acid is an AHA and is selected from the group consisting of lactic acid and glycolic acid.

E. The composition of paragraph B, wherein the acid is a PHA and is lactobionic acid or glucolactone.

F. The composition of any one of paragraphs A to E, wherein the composition is free of a dicarboxylic acid or a multi-carboxylic acid.

G. The composition of paragraph B, wherein the mole ratio of the acid to the sum of the cationic surfactant and anti-dandruff active is from 1.0 to 2.0.

H. The composition of any one of paragraphs A to G, wherein the mole ratio of cationic surfactant to the anti-dandruff active is from 2.5 to 4.5.

I. The composition of any one of paragraphs A to H, wherein the mole ratio of cationic surfactant to the anti-dandruff active is from 3.0 to 4.0.

J. The composition of any one of paragraphs A to I, wherein the composition is free of silicone.

K. The composition of any one of paragraphs A to J, wherein the water-soluble polymer has a cationic charge.

L. The composition of any one of paragraphs A to K, wherein the water-soluble polymer is polyquaternium-10 or cetyl hydroxyethylcellulose.

M. The composition of any one of paragraphs A to L, further comprising a fragrance comprising hinokitiol, phenoxyethanol and L-menthol.

N. The composition of paragraph M, wherein the composition comprises from 0.01 to 0.1, by weight of the composition of hinokitiol, from 0.01 to 0.1, by weight of the composition, of phenoxyethanol, and from 0.01 to 0.2, by weight of the composition, of L-menthol.

O. The composition of any one of paragraphs A to N, further comprising a nonionic surfactant.

P. The composition of any one of paragraphs A to O, wherein the composition is substantially free of a preservative.

Q. The composition of any one of paragraphs A to P, wherein the composition is substantially free of a liquid oily compound having an A log P greater than 5.5.

R. The composition of any one of paragraphs A to Q, wherein the cationic surfactant is stearamidopropyl dimethylamine.

S. A hair care composition comprising: a) a substituted 2-pyridinol-N-oxide material; b) a cationic surfactant having melting point higher than 40° C.; c) a fatty alcohol having a melting point higher than 40° C.; d) a water-soluble polymer; e) water; and f) a monocarboxylic acid; and wherein the composition is free of a silicone, a sulfate, an acrylate, and a preservative.

T. A translucent hair care composition comprising: a) a substituted 2-pyridinol-N-oxide material; b) a cationic surfactant having melting point higher than 40° C.; c) a fatty alcohol having a melting point higher than 40° C.; d) a water-soluble polymer; e) water; and f) one of glutamic acid or aspartic acid; wherein the composition has a pH from about 3.5 to about 6.0; wherein the composition has a light transmittance percent measured at 600 nm greater than 10%; and wherein the viscosity is from about 10 Pa·s to about 100 Pa·s.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A translucent hair care composition comprising:
   a) a substituted 2-pyridinol-N-oxide material;
   b) about 1.24% to about 3.24% stearamidopropyl dimethylamine (SAPDMA), wherein a weight ratio of SAPDMA to the substituted 2-pyridinol-N-oxide material is 2.4:1 to 6.2:1;
   c) a fatty alcohol having a melting point higher than 40° C.;
   d) a water-soluble polymer, wherein the water-soluble polymer has a natural origin backbone selected from the group consisting of cellulose, starch, guar, and gellan;
   e) water; and
   f) a monocarboxylic acid;
   wherein the composition has a pH of about 3.5 to about 6.0;
   wherein the composition has a light transmittance of greater than 10%, when measured at 600 nm; and
   wherein the composition has a viscosity of about 10 Pa-s to about 100 Pa-s.

2. The composition of claim 1, wherein the monocarboxylic acid is selected from the group consisting of an α-hydroxy acid (AHA), a β-hydroxy acid (BHA), a polyhydroxy acid (PHA), and an aminoacid.

3. The composition of claim 2, wherein the monocarboxylic acid is a BHA and is salicylic acid.

4. The composition of claim 2, wherein the monocarboxylic acid is an AHA and is selected from the group consisting of lactic acid and glycolic acid.

5. The composition of claim 2, wherein the monocarboxylic acid is a PHA and is lactobionic acid or gluconolactone.

6. The composition of claim 1, wherein the composition is free of a dicarboxylic acid or a multi-carboxylic acid.

7. The composition of claim 1, wherein the mole ratio of the monocarboxylic acid to the sum of the cationic surfactant and substituted 2-pyridinol-N-oxide material is 1.0 to 2.0.

8. The composition of claim 1, wherein the composition is free of silicone.

9. The composition of claim 1, wherein the water-soluble polymer has a cationic charge.

10. The composition of claim 1, wherein the water-soluble polymer is polyquaternium-10 or cetyl hydroxyethylcellulose.

11. The composition of claim 1, further comprising a fragrance comprising hinokitiol, phenoxyethanol and L-menthol.

12. The composition of claim 11, wherein the composition comprises 0.01% to 0.1%, by weight of the composition of hinokitiol, 0.01% to 0.1%, by weight of the composition, of phenoxyethanol, and 0.01% to 0.2%, by weight of the composition, of L-menthol.

13. The composition of claim 1, further comprising a nonionic surfactant.

14. The composition of claim 1, wherein the composition is substantially free of a preservative.

15. The composition of claim 1, wherein the composition is substantially free of a liquid oily compound having an A log P greater than 5.5.

* * * * *